United States Patent
Ludin et al.

(10) Patent No.: US 8,123,714 B2
(45) Date of Patent: Feb. 28, 2012

(54) PROGRAMMABLE SHUNT WITH ELECTROMECHANICAL VALVE ACTUATOR

(75) Inventors: Lev Ludin, Newton, MA (US); Christopher Mauge, Doylestown, PA (US)

(73) Assignee: Codman & Shurtleff, Inc., Raynham, MA (US)

( * ) Notice: Subject to any disclaimer, the term of this patent is extended or adjusted under 35 U.S.C. 154(b) by 649 days.

(21) Appl. No.: 11/771,015

(22) Filed: Jun. 29, 2007

(65) Prior Publication Data

US 2009/0005720 A1    Jan. 1, 2009

(51) Int. Cl.
*A61M 5/00* (2006.01)

(52) U.S. Cl. .............................. 604/9; 604/8
(58) Field of Classification Search ............. 604/8, 9, 604/264

See application file for complete search history.

(56) References Cited

U.S. PATENT DOCUMENTS

| | | | |
|---|---|---|---|
| 3,886,948 A * | 6/1975 | Hakim ............................. | 604/9 |
| 4,332,255 A | 6/1982 | Hakim et al. | |
| 4,387,715 A | 6/1983 | Hakim et al. | |
| 4,443,214 A | 4/1984 | Marion | |
| 4,551,128 A | 11/1985 | Hakim et al. | |
| 4,595,390 A | 6/1986 | Hakim et al. | |
| 4,615,691 A | 10/1986 | Hakim et al. | |
| 4,772,257 A | 9/1988 | Hakim et al. | |
| 5,637,083 A | 6/1997 | Bertrand et al. | |
| 5,643,194 A | 7/1997 | Negre | |
| 5,704,352 A | 1/1998 | Tremblay et al. | |
| 5,928,182 A | 7/1999 | Kraus et al. | |
| 6,264,625 B1 * | 7/2001 | Rubenstein et al. ............. | 604/9 |
| 6,336,924 B1 * | 1/2002 | Lecuyer et al. ................ | 604/540 |
| 6,533,733 B1 * | 3/2003 | Ericson et al. ................ | 600/561 |
| 6,585,677 B2 * | 7/2003 | Cowan et al. .................... | 604/9 |
| 6,702,249 B2 | 3/2004 | Ito | |
| 6,840,917 B2 | 1/2005 | Marion | |
| 6,926,691 B2 * | 8/2005 | Miethke ........................... | 604/9 |
| 2001/0002250 A1 | 5/2001 | Burbank et al. | |
| 2002/0026139 A1 | 2/2002 | Bertrand et al. | |

(Continued)

FOREIGN PATENT DOCUMENTS

EP    0 982 048 A    3/2000

(Continued)

OTHER PUBLICATIONS

Search Report for EP 06 25 3362, dated Sep. 18, 2006.

*Primary Examiner* — Leslie Deak
(74) *Attorney, Agent, or Firm* — Nutter McClennen & Fish LLP

(57) ABSTRACT

Devices and methods for regulating and directing bodily fluids from one region of a patient to another region are disclosed. In general, an apparatus is provided that can include an implantable shunt system and a system controller. The implantable shunt system can have an adjustable valve for regulating the flow of fluid, a sensor element for measuring a physiological characteristic of a patient, and an electromechanical valve actuator that can be adapted to adjust a resistance of the valve. The implantable shunt system can be in electrical communication with the system controller. The system controller can generally be adapted to receive a physiological characteristic of the patient and operate the electromechanical valve actuator to adjust a resistance of the valve. The apparatus can also include an external programming device that is in communication with the system controller.

33 Claims, 7 Drawing Sheets

U.S. PATENT DOCUMENTS

| | | |
|---|---|---|
| 2002/0058901 A1 | 5/2002 | Marion |
| 2004/0010219 A1 | 1/2004 | McCusker |
| 2004/0143242 A1 | 7/2004 | Ludin et al. |
| 2005/0010159 A1 | 1/2005 | Reich et al. |
| 2005/0092335 A1 | 5/2005 | Bertrand et al. |
| 2006/0020239 A1 | 1/2006 | Geiger et al. |

FOREIGN PATENT DOCUMENTS

| | | |
|---|---|---|
| EP | 1738792 A1 | 1/2007 |
| WO | WO-0247754 A1 | 6/2002 |

\* cited by examiner

PROGRAMMABLE SHUNT WITH ELECTROMECHANICAL VALVE ACTUATOR

FIELD OF THE INVENTION

The present invention relates to methods and devices for regulating and directing bodily fluids from one region of a patient to another region.

BACKGROUND OF THE INVENTION

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain becomes blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the brain's ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve, and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the blood stream.

Generally, the shunt valve, which can have a variety of configurations, is effective to regulate the flow rate of fluid through the shunt system. In some shunt valve mechanisms, the fluid flow rate is proportional to the pressure difference at the valve mechanism. These shunt valve mechanisms permit fluid flow only after the fluid pressure has reached a certain threshold level. Thus, when the fluid pressure is slightly greater than the threshold pressure level, the fluid flow rate is relatively low, but as the pressure increases, the fluid flow rate simultaneously increases. Typically, the shunt valve allows fluid to flow normally until the intracranial pressure has been reduced to a level that is less than the threshold pressure of the shunt valve, subject to any hysteresis of the device.

Certain conventional shunt valves allow external adjustment of the threshold pressure level at which fluid flow will commence to avoid invasive surgical procedures. In some shunt systems, the shunt valve contains a magnetized rotor to control the pressure threshold of the valve. Physicians can then use an external adjustment mechanism, such as a magnetic programmer, to adjust the pressure threshold of the shunt valve. However, these magnetized rotors can be unintentionally adjusted in the presence of a strong external magnetic field, such as during an MRI procedure. Unintentional adjustment of the pressure threshold could lead to either the overdrainage or underdrainage of CSF, which can result in dangerous conditions, such as subdural hematoma.

Attempts have been made to provide a locking mechanism that prevents unintentional valve adjustment, even in the presence of a strong external magnetic field, while simultaneously allowing intentional adjustment of the pressure threshold. One such approach has been detailed in U.S. Pat. No. 5,643,194, in which Negre describes a locking means having two opposed micro-magnets mounted on the rotor. In the presence of a bi-directional magnetic field, these micro-magnets move linearly in the rotor, in a substantially radial direction, to activate the locking means. However, the Negre locking means does not eliminate the risk of inadvertent valve adjustment in the presence of a strong external magnetic field.

Another approach has been described in U.S. Pat. No. 5,637,083, in which Bertrand et al. describe a valve that includes means for locking the rotor assembly in a desired position. This locking means uses a pin having a first end adapted to engage a series of detents in an outer peripheral surface of the rotor assembly, thereby preventing the rotor assembly from rotating. The locking means is disengaged by a pin-actuating means having two levers that move the pin from a first, extended position, i.e., within the detent(s) in the outer peripheral surface, to a second, retracted position. The first lever is a pivotable lever having a shaft adapted to engage a second end of the pin, while the second lever is a manually actuated lever that is biased to urge the pin into the first, extended position. This manually actuated lever, however, is located within the valve chamber that is used to pump, or flush, fluid from the shunt valve. Thus, by virtue of its location within the pumping chamber, the manually actuated lever, and consequently the pin-actuating means, can impair or inhibit the function of the pumping chamber.

Accordingly, a need exists for improved methods and devices for regulating cerebrospinal fluid flow.

SUMMARY OF THE INVENTION

Devices and methods for regulating and directing bodily fluids from one region of a patient to another region are disclosed. In general, an apparatus is provided that can include an implantable shunt system and a system controller. While a variety of configurations are available for the implantable shunt system, in one exemplary embodiment, the system can have an adjustable valve for regulating the flow of fluid, a sensor element for measuring a physiological characteristic of a patient, and an electromechanical valve actuator that can be adapted to adjust a resistance of the valve. The implantable shunt system can be in electrical communication with the system controller. The system controller can generally be adapted to receive a physiological characteristic of the patient and operate the electromechanical valve actuator to adjust a resistance of the valve. In one exemplary embodiment, the sensor element can be a pressure sensor for detecting a cerebro-spinal fluid pressure. In another embodiment, the shunt system can include a second sensor element for measuring an additional physiological characteristic. The apparatus can be battery powered (i.e., by a battery contained therein) or can be powered by an external component.

In one exemplary embodiment, the valve can take the form of a ball valve that is operatively associated with an electromechanical valve actuator. While several configurations are available for the electromechanical valve actuator, in general, the actuator can include a spring and a pressure setting mechanism. A variety of springs can be used with the valve actuator including, for example, leaf and helical springs. The pressure setting mechanism can also have a variety of configurations. For example, in one embodiment, the pressure setting mechanism can include a motor driven rotor assembly that is adapted to adjust a resistance of the valve upon actuator of the motor. In another exemplary embodiment, the pressure setting mechanism includes a motor driven stop member that is adapted to apply a force to the spring to adjust a resistance of the valve.

In general, the system controller can be adapted to receive a physiological characteristic of the patient and operate the electromechanical valve actuator to adjust a resistance of the valve. In one exemplary embodiment, the system controller can include a microprocessor for comparing measured values to predetermined target values. For example, where the sensor element is a pressure sensor, the microprocessor can be adapted to compare the measured pressure detected by the sensor element to a predetermined target pressure. To facilitate the comparison, the system controller can also be configured to receive an input signal representative of a target value. In addition to comparing values, the microprocessor can be programmed to calculate a desired resistance for the valve to achieve a target pressure. A variety of configurations are available for the system controller, including, for example, configurations in which the controller is contained within the implantable shunt system and configurations in which the controller is disposed on an implant separate from the shunt system.

The apparatus for regulating fluid flow can further include an external programming device that is in communication with the system controller. In general, the programming device can include a user input element that allows an operator to input one or more instructions to be communicated to the system controller. For example, the external programming device can be adapted to transmit a signal to the system controller that is representative of a predetermined target value for the CSF pressure of a patient. The external programming device can have a variety configurations and in one exemplary embodiment can include a display element for communicating a physiological characteristic to a user. In addition to communicating instructions to the system controller, the programming device can also be adapted to power the implantable shunt system.

In one exemplary embodiment, the implantable shunt system, system controller, and external programming device can be configured to communicate via radiofrequency (RF) communication. In an exemplary embodiment, the shunt system, system controller, and programming device can include signal transmitters/receivers or antennas that can be configured to send and/or receive signals from one another. Such communication can provide non-invasive control of the electromechanical valve actuator. The antennas can have a variety of configurations as well as be disposed at various locations in the system. For example, in one exemplary embodiment, both the system controller and antenna associated therewith can be disposed on the implantable shunt system. In another embodiment, the controller can be contained within the implantable shunt system but the antenna can be disposed on a separate implant. In yet another exemplary embodiment, both the system controller and antenna associated therewith can be disposed on an implant that is separate from the shunt system.

Methods of regulating cerebrospinal fluid flow are also provided. In general, the method can include comparing a target value to a value detected by a sensor associated with an implantable shunt system, and activating an electromechanical valve actuator of the implantable shunt system to adjust a resistance of a valve of the shunt system if the detected value is not equal to the target value. The method can also include inputting one or more target values to an external programming device and transmitting those values to a system controller of the implantable shunt system. In one exemplary embodiment, any of the above steps can be repeated until the detected value is equal to the target value.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
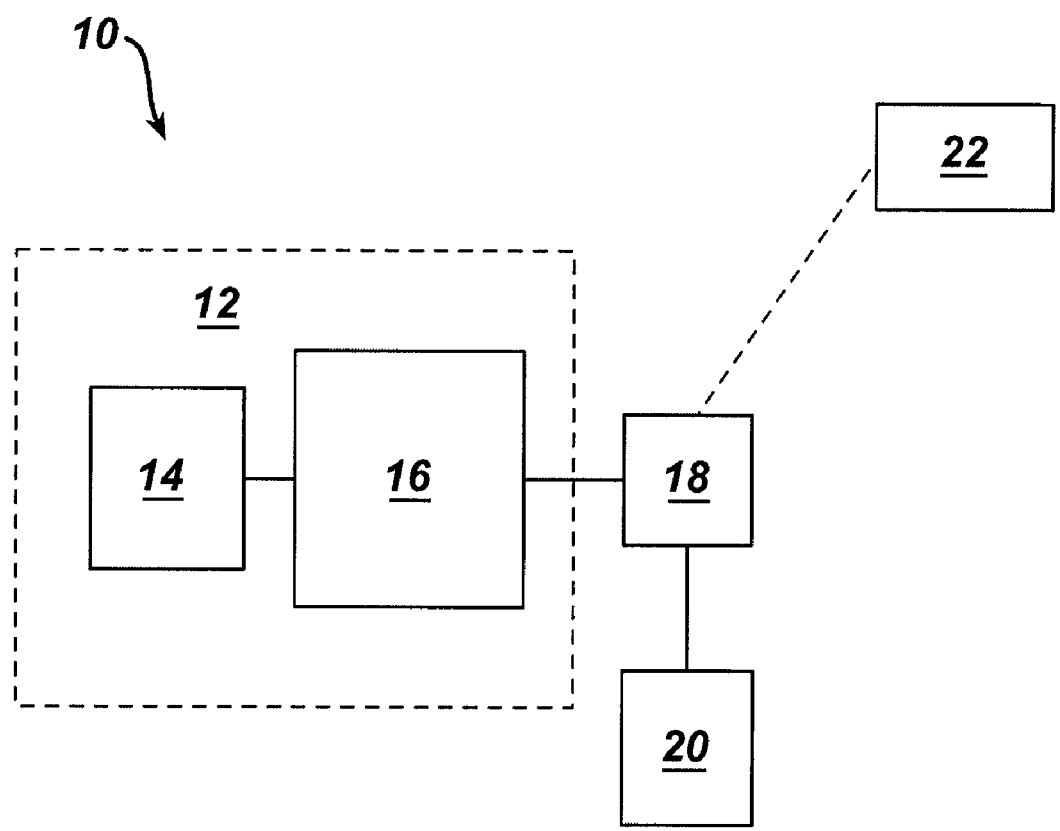
FIG. 1 is a diagrammatic view of a system of the invention.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Methods and devices for regulating and directing bodily fluids from one region of a patient to another region are disclosed. In general, an apparatus 10 (illustrated in FIG. 1) is provided that can include an implantable shunt system 12 and a system controller 18. While a variety of configurations are available, in one exemplary embodiment, the apparatus 10 can have an adjustable valve 14 for regulating the flow of fluid, a sensor element 20 for measuring a physiological characteristic of a patient, and an electromechanical valve actuator 16 that can be adapted to adjust a resistance of the valve. As used herein, "electromechanical actuator" includes mechanical systems (or mechanisms) that are actuated or controlled electrically such as, but not limited to, electric motors, solenoids, and linear actuators. The implantable shunt system can be in electrical communication with the system controller 18 which may or may not be provided within the shunt system housing. The system controller 18 can generally be adapted to receive a physiological characteristic of the patient from the sensor 20 and operate the electromechanical valve actuator 16 to adjust a resistance of the valve 14. The system controller 18 may also receive instructions from an external programming device 22. The apparatus can be battery powered (i.e., by a battery contained therein) or can be powered by an external component.

Although the device is shown and described as regulating the flow of cerebrospinal fluid (CSF), one skilled in the art will appreciate that the device can be used to regulate the flow of any bodily fluid.

Figure 1A:
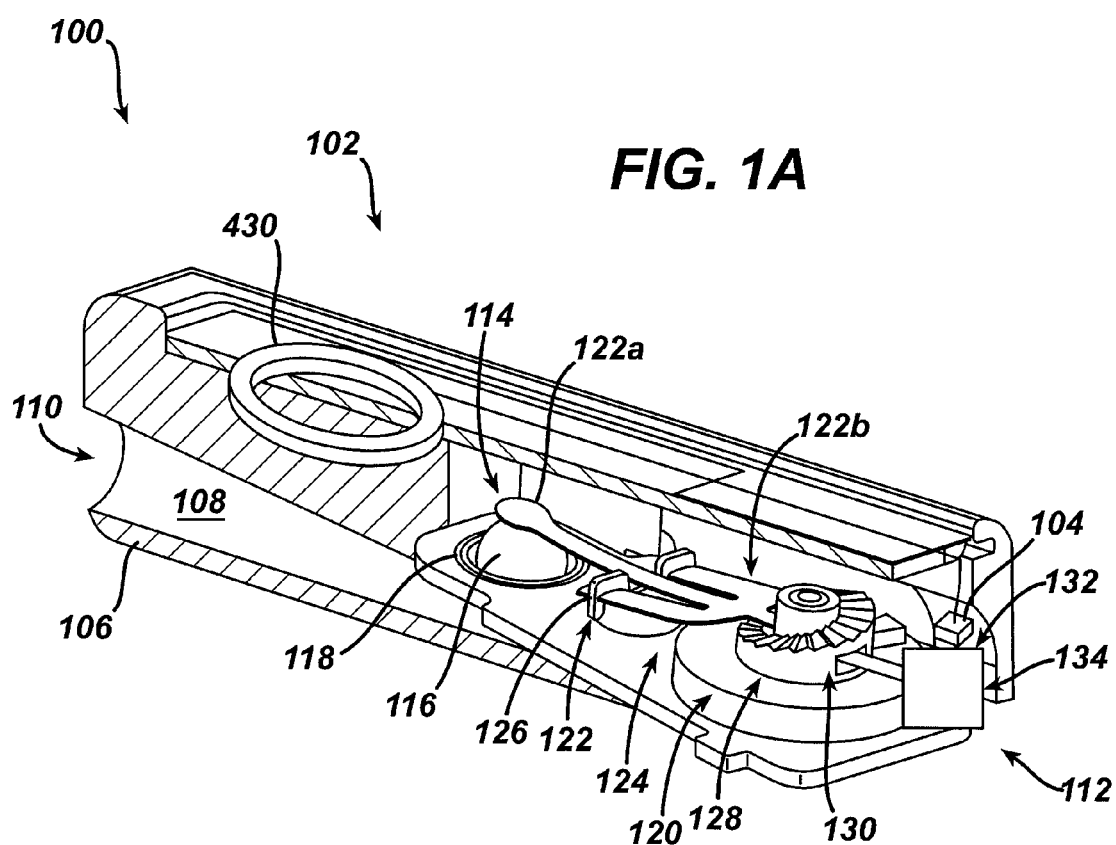
FIG. 1A is a cross-sectional perspective view of one embodiment of an apparatus for regulating fluid flow.
Figure 4:
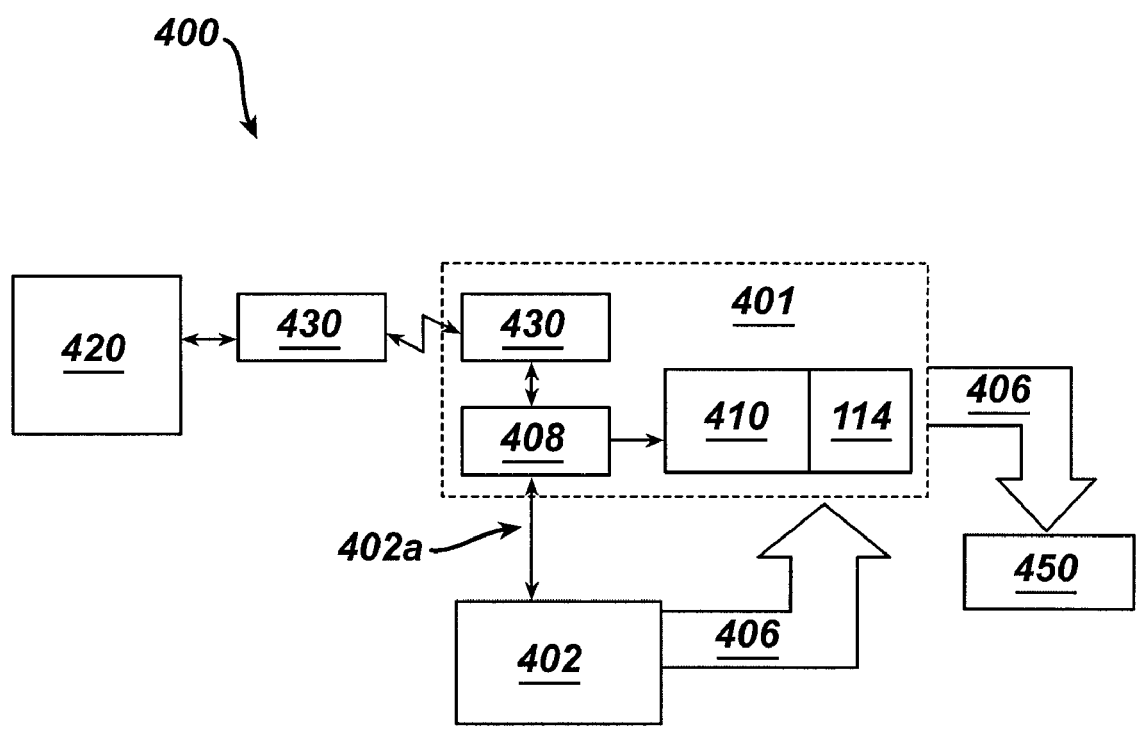
FIG. 4 is a schematic view of one embodiment of a shunt valve assembly for regulating fluid flow.
Figure 5:
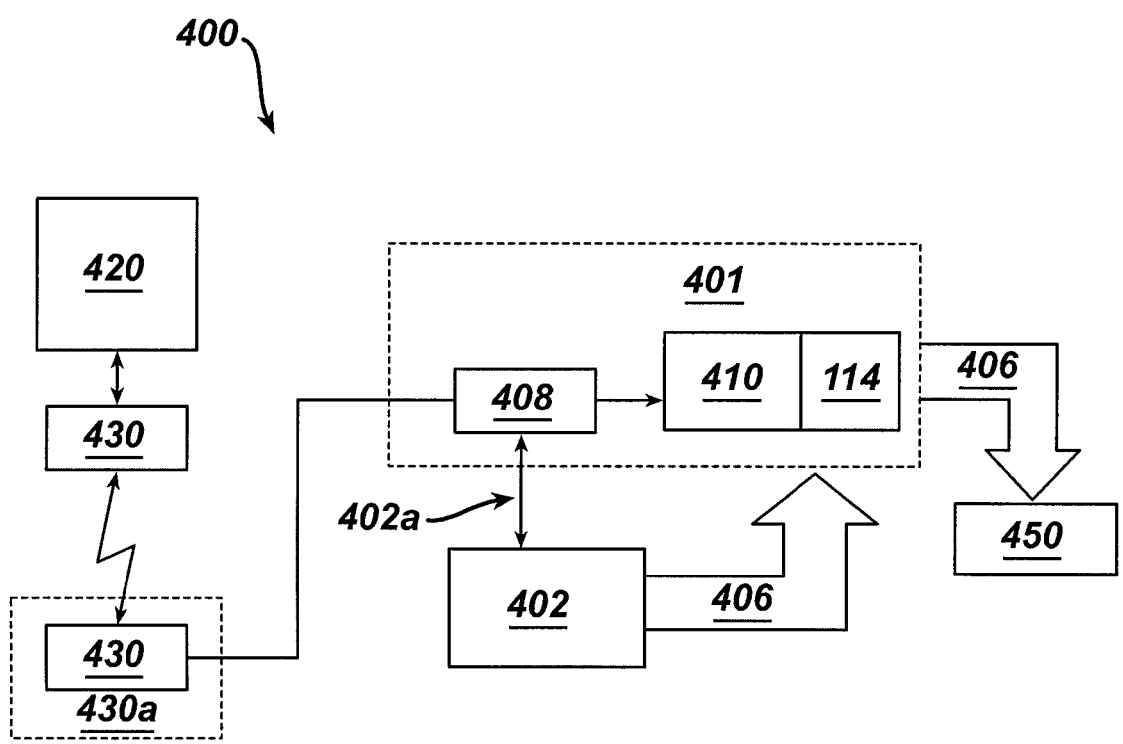
FIG. 5 is a schematic view of another embodiment of a shunt valve assembly for regulating fluid flow.
Figure 6:
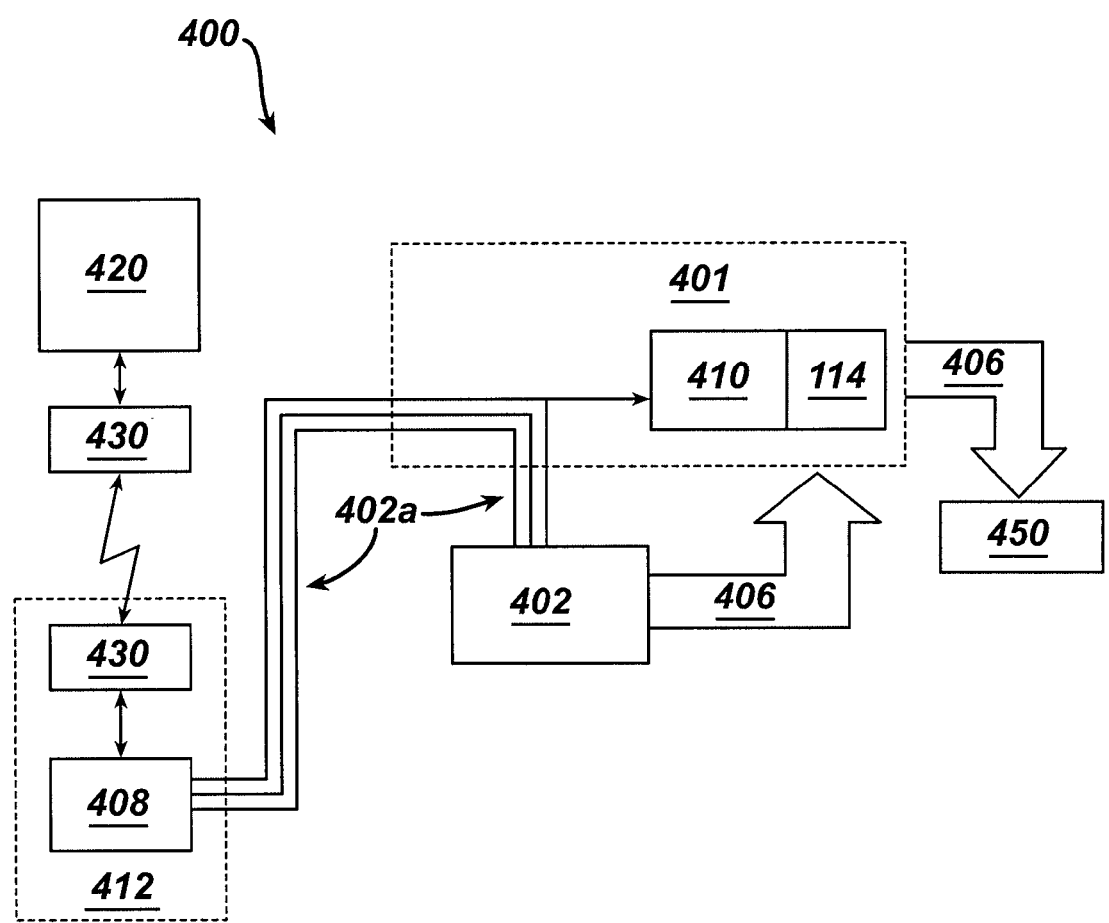
FIG. 6 is a schematic view of another embodiment of a shunt valve assembly for regulating fluid flow.

FIG. 1A illustrates one exemplary embodiment of an apparatus 100 for regulating fluid flow. As indicated above, the apparatus can generally include an implantable shunt system 102 and a system controller 104. The shunt system 102 can be adapted to drain excess fluid from one area of a patient's body and direct the fluid to another site in the body. A variety of configurations are available for the shunt system 102. As used herein, a shunt refers to any device that diverts a flow of fluid. A person of ordinary skill in the art will recognize that a variety of configurations for shunt devices are possible. In one exemplary embodiment, shown in FIG. 1A, the shunt system 102 includes a housing 106 defining an inlet port 110, an outlet port 112, and a chamber 108 oriented between the inlet port 110 and the outlet port 112. The inlet and outlet ports 110, 112 can be coupled to inlet and outlet or drainage catheters 450, respectively (FIGS. 4-6). For example, in one embodiment, the apparatus can be used to treat hydrocephalus and the inlet catheter is inserted within a ventricle of a patient's brain and the drainage catheter is inserted within another area of the patient's body, such as the peritoneum. During operation, the shunt system 102 can carry CSF, originating from the ventricle, from the inlet catheter, through the chamber, and to the drainage catheter.

The implantable shunt system 102 can also include an adjustable valve 114 for regulating the flow of fluid. The resistance of the valve 114 can be adjusted within the housing 106 to set a pressure threshold at which excess CSF begins to flow from the ventricle of a brain through the valve 114 and to another area of a patient's body. While the valve 114 can have several configurations, in an exemplary embodiment, shown in FIG. 1A, the valve 114 takes the form of a ball valve. As shown, the ball 116 is disposed in the chamber 108 of the housing 106 and is seated in a circular orifice 118. Although the valve 114 is shown and described as a ball valve, one skilled in the art will appreciate that a number of valve configurations are available for use with the implantable shunt system 102. The ball 116 can act as a stop member and regulate the fluid flow through the shunt system 102. For example, fluid can be prevented from flowing through the shunt system when the ball 116 is fully seated within the circular orifice 118. Alternatively, fluid can be allowed to flow through the shunt system 102 when the pressure in the ventricle exceeds the force being applied to the ball 116 to seat it in the circular orifice 118. Thus, varying the force applied to the ball 116 can be effective to vary the resistance of the valve 114 (i.e., the pressure threshold at which fluid begins to flow through the valve 114).

Figure 2:
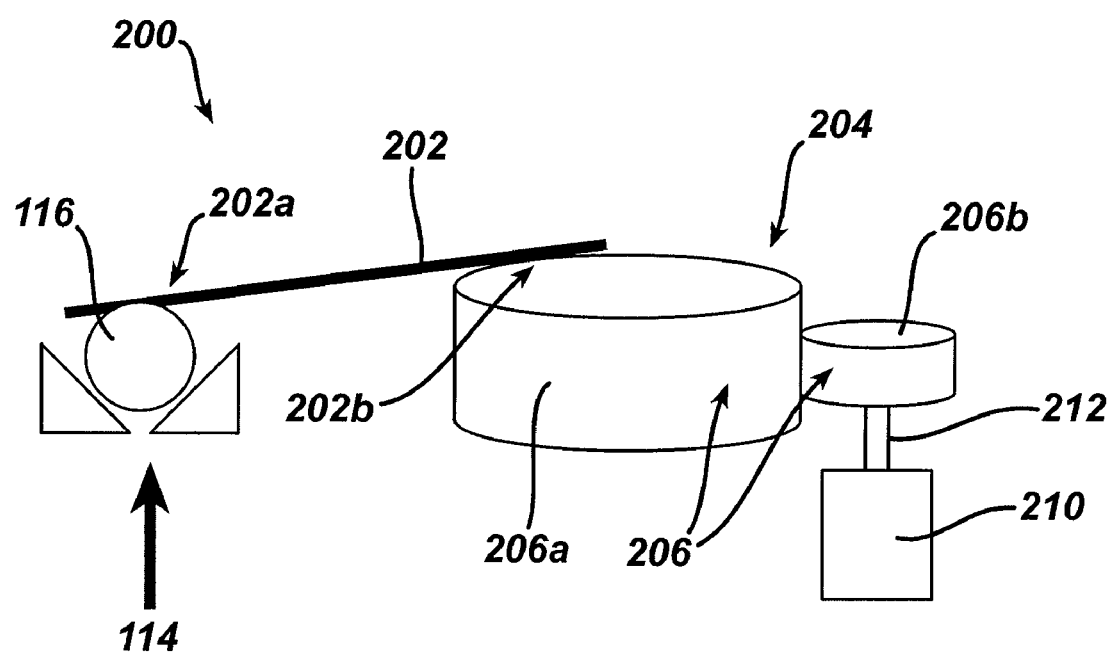
FIG. 2 is a schematic view of one embodiment of an electromechanical valve actuator.
Figure 3:
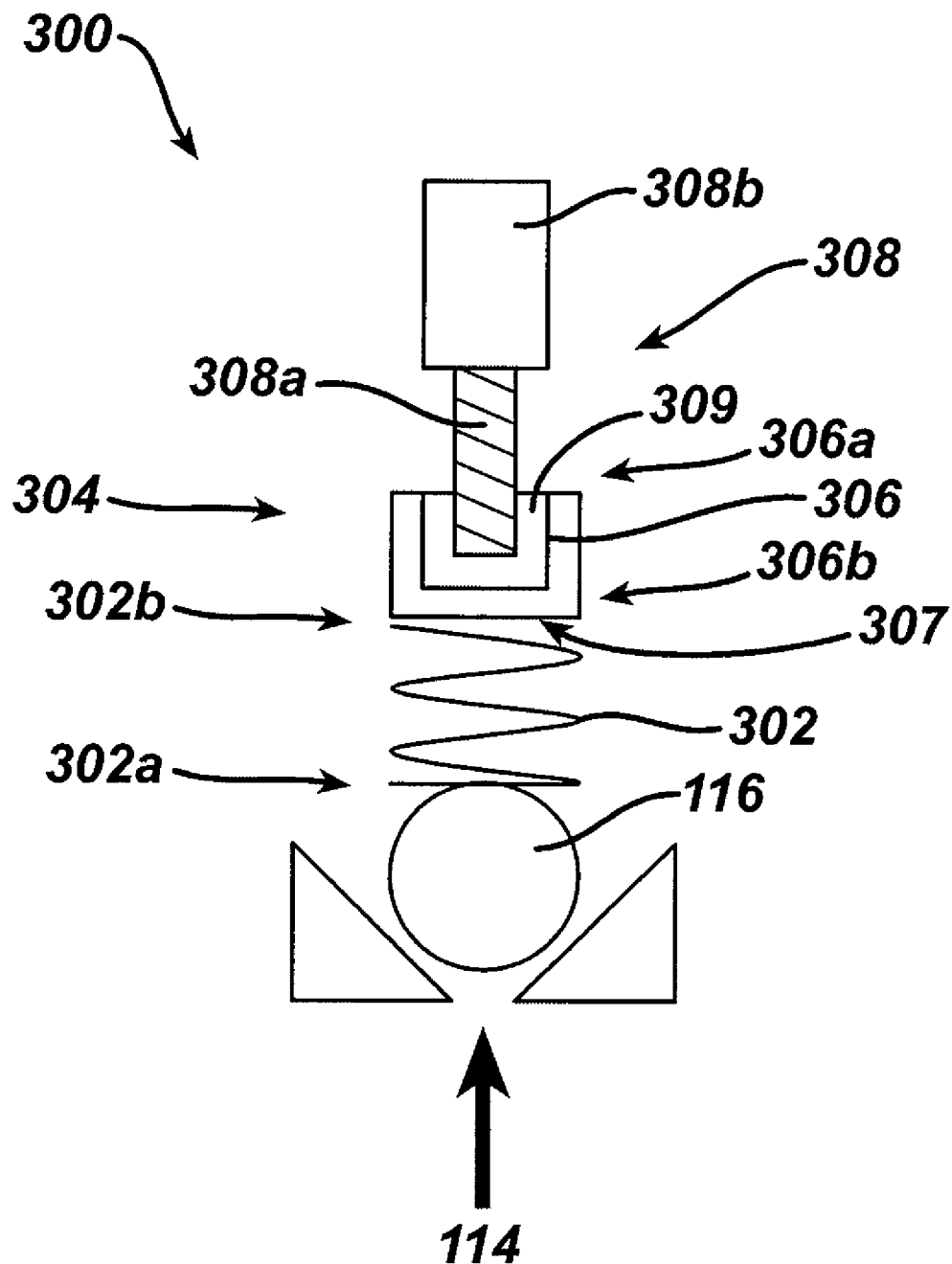
FIG. 3 is a schematic view of another embodiment of an electromechanical valve actuator.

A variety of techniques can be used to adjust the resistance of the valve 114. For example, in one exemplary embodiment, an electromechanical valve actuator 120 can be operatively associated with the valve 114 and adapted to adjust a resistance of the valve 114. The electromechanical valve actuator 120 can be configured to adjust and maintain the pressure threshold at which fluid begins to flow through the valve 114 thereby reducing the risk of either over- or under-drainage of CSF from a brain ventricle. The electromechanical valve actuator 120 can generally include a spring 122 and a pressure setting mechanism 124. The electromechanical valve actuator 120 can effectively prevent movement of the valve 114, such as when the shunt system is exposed to environmental magnetic forces. In certain cases, for example, the shunt system 102 can be subjected to a strong external magnetic field, such as when a patient having an implanted shunt system 102 undergoes an magnetic resonance imaging (MRI) procedure. The magnetic field generates a force on the shunt system 102 that can induce motion of the pressure setting mechanism 124 and can cause the pressure setting mechanism 124 to adjust the position of the valve 114. The electromechanical valve actuator 120, however, can lock the valve 114 in place to maintain a set pressure threshold within the shunt system 102 when exposed to the magnetic field. FIGS. 1-3 illustrate a variety of exemplary embodiments of electromechanical valve actuators 120 for use with the shunt system 102 described herein. One skilled in the art will appreciate that various springs and configurations of pressure setting mechanisms can form the electromechanical valve actuator, and the actuator should not be limited to the features and configurations described below.

As shown, the electromechanical valve actuator 120 includes a leaf spring 122 that is coupled to a pressure setting mechanism 124 having a cantilever 126 and a rotor assembly 128. As indicated above, the ball 116 of the ball valve can regulate the fluid flow through the shunt system. The ball 116 can be operatively joined to a first end 122a of the cantilevered spring 122 which a second end 122b of the spring 122 can engage a stair array 130 of the rotor assembly 128. In this embodiment, the rotor assembly 128 can include the stair-step array 130 in the form of a spiral staircase to provide pressure settings in discrete steps. The rotor assembly 128 can also include an actuation mechanism 132 that is configured to rotate the stair array 130 with respect to the cantilevered spring 122. In general, the mechanism 132 can include a motor 134 that is operatively associated with the stair array 130. For example, in one exemplary embodiment, shown in FIG. 1A, the mechanism 132 includes a micro-motor 134 that is coupled to the stair array 130 via gear teeth provided on each (not shown). A variety of motors can be used to rotate the stair array 130 including, but not limited to, micro-motors, stepper-motors, and piezo-motors.

In use, the actuation mechanism 132 of electromechanical valve actuator 120 can rotate the spiral stair array 130 with respect to the cantilevered spring 122, and the second end 122b of the spring 122 can move up or down each stair of the array 130. Moving the second end 122b of the spring 122 up or down can be effective to change the angle of deflection of the spring 122 (e.g., relative to the cantilever 126). The change in the angle of deflection of the spring 122, in turn, alters the force that is exerted by the spring 122 on the ball 116. As indicated above, changing the force applied to the ball 116 can result in a corresponding increase or decrease of the established pressure threshold at which fluid begins to flow through the shunt system 102.

An antenna 430 can also be provided to allow for non-invasive control of the electromechanical valve actuator 120. As is described below in detail, one or more antennas 430 can have a variety of configurations as well as be disposed at various locations throughout the system. Referring generally to FIG. 1, the shunt system 12, system controller 18, and programming device 22 can include signal transmitters/receivers or antennas 430 that can be configured to send and/or receive signals from one another to allow the individual components of the apparatus 10 to communicate with each other as well as facilitate non-invasive control of the apparatus 10.

FIG. 2 illustrates another exemplary embodiment of an electromechanical valve actuator 200 for use with the implantable shunt system 102. As shown, the electromechanical valve actuator 200 includes a leaf spring 202 that is operatively associated with a pressure setting mechanism 204 that takes the form of a gear assembly 206. Similar to the embodiment shown in FIG. 1A, a first end 202a of the leaf spring 202 can be operatively associated with the ball 116 of the ball valve and a second end 202b of the spring 202 can engage the gear assembly 206. The gear assembly 206 can include first and second gears 206a, 206b. The first gear 206a can have a series of helical steps (not shown) formed thereon and can be adapted to engage the spring 202. The second gear 206b can engage the first gear 206a as well as be operatively associated with an actuation mechanism 208 of the gear assembly 206. The actuation mechanism 208 can be configured to drive the gears 206a, 206b and rotate the helical steps with respect to the spring 202. The mechanism 208 shown in FIG. 2 includes a micro-motor 210 that is coupled to the second gear 206b via a cylindrical motor shaft 212. As indicated above, a variety of motors can be used to rotate the stair array including, but not limited to, micro-motors, stepper-motors, and piezo-motors. In use, the actuation mechanism 208 can drive the gear assembly 206 to rotate the helical steps with respect to the spring 202 and move the second end 202b of the spring 202 up or down the steps. As described above, such movement can be effective to change in the angle of deflection of the spring 202 thereby altering the force that is exerted on the ball 116 and increasing or decreasing the established pressure threshold at which fluid begins to flow through the shunt system.

Another exemplary embodiment of an electromechanical valve actuator 300 is shown in FIG. 3. As shown, the electromechanical valve actuator 300 includes a helical spring 302 that is coupled to a pressure setting mechanism 304 having a stop member 306 and motor assembly 308. A first end 302a of the helical spring 302 can engage the ball 116 of the ball valve, and a second end 302b of the spring 302 can abut a distal facing surface 307 of the stop member 306. The stop member 306 can have virtually any configuration, for example, as shown in FIG. 3, the stop member 306 is a generally cylindrical cap that has a closed distal end 306b and an open proximal end 306a with a bore 309 formed therein. The bore 309 can be threaded and adapted to receive and engage a threaded shaft 308a of the motor assembly 308. A motor 308b, such as one described above, can drive the threaded shaft 308a to move the stop member 306 in the proximal and/or distal directions. The closed distal end 306b of the stop member 306 can be configured to apply a force to the spring 302 such that distal movement of the stop member 306 is effective to compress the spring 302 and alter the force that is exerted by the spring 302 on the ball 116. As indicated above, changing the force applied to the ball 116 can result in a corresponding increase or decrease of the established pressure threshold at which fluid begins to flow through the shunt system.

The implantable shunt system can further include a sensor element for measuring a physiological characteristic of a patient. The sensor element can be coupled to the valve or it can be separate from the valve. For example, as shown in FIGS. 4-6, the sensor element 402 is in electrical communication with the shunt system 401 and is coupled to the system via wires 402a. Additionally, while the sensor element 402 is shown as being positioned within the CSF flow pathway 406 of the shunt system 401, in another exemplary embodiment, the sensor element 402 can be located outside of the CSF flow pathway 406 though still residing within the ventricular cavity of the patient. The sensor element 402 can be configured to measure a variety of physiological characteristics of a patient including, but not limited to, CSF pressure. Although the shunt system 401 is shown as having a single sensor element 402, one skilled in the art will appreciate that the system can include multiple sensor elements having several different configurations. For example, in one embodiment, the system 401 can include multiple pressure sensors to measure the CSF pressure at various points in the ventricular cavity. In another exemplary embodiment, the system 401 can include multiple sensor elements each configured to measure a different physiological characteristic of a patient.

As indicated above, the apparatus 400 for regulating fluid flow can also include a system controller 408. In general, the controller 408 can be in electrical communication with the implantable shunt system 401 and can be adapted to receive the physiological characteristic measured by the sensor element 402 and to operate the electromechanical valve actuator 410 to adjust a resistance of the valve 114. For example, the system controller 408 can be configured to receive an input signal that is generated by the sensor element 402 and is representative of the measured value of the physiological characteristic (e.g., the CSF pressure). The system controller 408 can also be configured to generate and transmit to the electromechanical valve actuator 410 an output control signal that commands the actuator 410 to adjust the resistance of the valve 114. A variety of configurations are available for the system controller 408. For example, as shown in FIGS. 4 and 5, in one exemplary embodiment, the controller 408 is contained within the implantable shunt system 401. Depending on the size and configuration of the electromechanical valve actuator 410, it may not be desirable to have the controller 408 contained within the shunt system 401. Accordingly, in another exemplary embodiment, the controller 408 can be disposed on an implant 412 that is separate from the implantable shunt system 401 (FIG. 6).

The system controller 408 can also include a processing unit such as, for example, a microprocessor, which enables the controller 408 to compare the measured physiological characteristic (e.g., the measured CSF pressure) detected by the sensor element 402 to a predetermined target value for the physiological characteristic. The predetermined target value can be ascertained through clinical assessment of the patent and is therefore customized for each particular patient. This target value can then be preset or programmed into the system controller 408. In use, the system controller 408 can operate according to an algorithm which determines whether the value measured by the sensor element 402 is higher than, lower than, or within an acceptable range of the target value. Based on this assessment, the algorithm can then determine whether the resistance of the valve 114 should be increased, decreased, or maintained in order to achieve the target CSF pressure for the patient. For example, where the physiological characteristic being measured is CSF pressure, the valve's resistance can be decreased if the measured pressure is higher than the target pressure. Conversely, the resistance of the valve 114 can be increased if the measured pressure is lower than the target pressure. The microprocessor can then generate an output control signal to the electromechanical valve actuator 410 which commands the actuator 410 to adjust its current resistance to the desired resistance. If the measured value is essentially the same as, or within an acceptable range of the target value, then the current resistance is maintained and no changes are made.

The apparatus 400 for regulating fluid flow can further include an external programming device 420 that is in communication with the system controller 408. In general, the programming device 420 can include a user input element that allows an operator to input one or more instructions to be communicated to the system controller 408. For example, the external programming device 420 can be adapted to transmit a signal to the system controller 408 that is representative of a predetermined target value for the CSF pressure of a patient. The external programming device 420 can have a variety configurations and in one exemplary embodiment can take the form of a hand-held remote control. The programming device 420 can include a display for communicating input and/or output values (e.g., the predetermined target value for a physiological characteristic being measured and/or the measured value of a physiological characteristic) to a user. In addition to communicating instructions to the system controller 408, the programming device 420 can also be adapted to power the implantable shunt system 401.

As indicated above, one or more antennas 430 can be provided to allow the individual components of the apparatus 400 to communicate with each other as well as facilitate non-invasive control of the apparatus 400. The implantable shunt system 401, system controller 408, and external programming device 420 can be equipped with electronic circuitry similar to those for medical telemetry systems that communicate physiological data (e.g., temperature, pressure, etc.) between an implant and a receiver unit. For example, the system controller 408 can be configured to generate an analog data signal that is then converted electronically to a digital pulse which is then transmitted by radiofrequency (RF) to the external programming device 420. As illustrated in FIGS. 4-6, the shunt system 401, system controller 408, and programming device 420 include signal transmitters/receivers or antennas 430 that can be configured to send and/or receive signals from one another. Such communication can provide non-invasive control of the electromechanical valve actuator 410. The antennas 430 can have a variety of configurations as well as be disposed at various locations in the system. For example, in one exemplary embodiment shown in FIG. 4, both the system controller 408 and antenna 430 associated therewith are disposed on the implantable shunt system 401. In another embodiment, shown in FIG. 5, the controller 408 is contained within the implantable shunt system 401 but the antenna 430 is disposed on a separate implant 430a. Such a configuration can allow for a larger, more powerful antenna to be placed in a more convenient location (e.g., a patient's arm rather than their head). In yet another exemplary embodiment, illustrated in FIG. 6, both the system controller 408 and antenna 430 associated therewith are disposed on an implant 412 separate from the implantable shunt system 401. Similar to the embodiment shown in FIG. 5, this embodiment can provide less restriction on the size of the system controller 408 and antenna 430, as these components are not part of the shunt system 401. One skilled in the art will recognize that these are merely examples of the forms of remote communication suitable for use with the fluid regulating apparatus 400 disclosed herein and a variety of other forms of non-invasive communication can be utilized without departing from the scope of the present invention.

Methods of regulating cerebrospinal fluid flow are also provided. In general, the method can include comparing a target value to a value detected by a sensor 402 associated with an implantable shunt system 401, and activating an electromechanical valve actuator 410 of the implantable shunt system 401 to adjust a resistance of a valve 114 of the shunt system 401 if the detected value is not equal to the target value.

In one exemplary embodiment, the method can include energizing the apparatus 400 with the external programming device 420 and detecting a physiological characteristic of a ventricular cavity (e.g., CSF pressure). The measured value can then be compared to a predetermined target value for that physiological characteristic. The predetermined target value can be preset in the system controller 408 or can be programmed in the controller via the external programming device 420. If the system controller 408 determines that the measured value is not equal to the target value, the controller 408 than determines whether the resistance for the valve 114 should be increased or deceased accordingly to achieve the predetermined target value for that physiological characteristic. The system controller 408 can then generate and transmit an activation signal to activate the electromechanical valve actuator 410 and adjust a resistance of the valve 114. If the measured value is essentially the same as, or within an acceptable range of the target value, then no change is made to the resistance of the valve 114.

During the operation of the external programming device 420 (i.e., when the device 420 is applied to the patient and the apparatus 401 is energized), data can be communicated between the device 420 and the system controller 408. For example, a user can input a target value to the programming device 420 and the device can communicate data representative of the target value to the system controller 408. Data can also be communicated between the implantable shunt system 401 and the system controller 408. The sensor element 402 can communicate data representative of the measured value of a physiological characteristic to the system controller 408, and the controller 408 can communicate a command to the electromechanical valve actuator 410 to adjust a resistance of the valve 114. More specifically, the system controller 408 can detect a value of a physiological characteristic measured by the sensor element 402 by receiving an input signal generated from the sensor element 402 that contains data about the measured value of the physiological characteristic. Similarly, the system controller 408 can adjust a resistance of the valve 114 by generating and transmitting an output control signal to the electromechanical valve actuator 410 that commands the actuator 410 to adjust a resistance of the valve 114.

In an application of the methods described above, if a patient experiences discomfort and/or pain, the apparatus 401 can be energized and data can be communicated from the external programming device 420 to the system controller 408. The apparatus 401 can be energized by either the patient himself or his attending physician. If the measured value is the same as, or falls within an acceptable range of the target value, then the system controller 408 is programmed to make no changes to the resistance. If, however, the system controller 408 detects that the measured value is higher or lower than the preset target value, the controller 408 sends a command to the electromechanical valve actuator 410 to adjust a resistance of the valve 114. Then, after some time has elapsed (e.g., a day, two days, a week, etc.) to allow the patient's physiology to respond to the valve's 114 new resistance setting, and the patient still experiences discomfort or pain, or simply wants to determine the current value of a particular physiological characteristic, the apparatus 401 can again be energized to measure the current value. If the system controller 408 does not detect a change in the measured value from the previous reading, the controller 408 can send another command to the electromechanical valve actuator 410 to adjust the resistance accordingly.

It is contemplated that the above steps can be repeated until an appropriate resistance is attained and the system controller 408 detects that the measured value is approaching or has approached the target value for that patient. For example, the above steps can be repeated whenever the patient begins to experience pain or discomfort. However, to safeguard against repeated or excessive valve 114 adjustments within a short window of time, which could produce deleterious health consequences for the patient, the system controller 408 can include a timed shutoff mechanism which would limit the user's ability to adjust the valve in a given time period. For example, the system controller's 408 valve adjustment features can be configured to deactivate after each use until a preset amount of time (e.g., a day, two days, a week, etc.) has passed whereby the valve adjustment feature is automatically reactivated. Such a safeguard ensures that a sufficient amount of time passes between adjustments so that the patient's physiology does not incur rapid CSF flow changes in a short amount of time. Of course, it is contemplated that the system controller 408 can still be capable of detecting a physiological characteristic of the patient's ventricular cavity even when the device's valve adjustment features are not active. Hence, the patient can continue to monitor a physiological characteristic of his ventricular cavity using the apparatus 401 even between stages of adjusting the valve 114.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An apparatus for regulating fluid flow, comprising:
   an implantable shunt system having:
      an adjustable valve for regulating the flow of fluid,
      a sensor element for measuring a physiological characteristic of a patient, and
      an electromechanical valve actuator adapted to adjust a resistance of the valve; and
   a system controller in electrical communication with the implantable shunt system and adapted to receive the physiological characteristic of the patient and operate the electromechanical valve actuator to adjust a resistance of the valve and thereby adjust a pressure threshold at which fluid begins to flow through the valve;
   further comprising an external programming device in communication with the system controller;
   wherein the external programming device includes a display for communicating the physiological characteristics of the patient to a user; and
   wherein the external programming device includes a user input element, the external programming device being configured to communicate one or more instructions to the system controller based on user input.

2. The apparatus of claim 1, wherein the valve is a ball valve.

3. The apparatus of claim 1, wherein the electromechanical valve actuator comprises a spring operatively associated with a pressure setting mechanism, and at least one selected from the group consisting of an electric motor, a solenoid, and a linear actuator mechanically coupled to the pressure setting mechanism to vary a pressure applied by the spring to thereby adjust the resistance of the valve.

4. The apparatus of claim 3, wherein the spring is a leaf spring.

5. The apparatus of claim 3, wherein the spring is a helical spring.

6. The apparatus of claim 3, wherein the pressure setting mechanism includes a motor driven rotor assembly adapted to adjust a resistance of the valve upon actuation of the motor.

7. The apparatus of claim 3, wherein the pressure setting mechanism includes a motor driven stop member, the stop member being adapted to apply a force to the spring to adjust a resistance of the valve.

8. The apparatus of claim 1, wherein the sensor element is a pressure sensor for detecting a cerebro-spinal fluid pressure.

9. The apparatus of claim 8, wherein the system controller includes a microprocessor for comparing the measured pressure detected by the sensor to a target pressure.

10. The apparatus of claim 9, wherein the system controller is configured to receive an input signal generated from the external programming device, the signal being representative of the target pressure.

11. The apparatus of claim 9, wherein the microprocessor is programmed to calculate a desired resistance for the valve to achieve the target pressure.

12. The apparatus of claim 1, wherein the controller is contained within the implantable shunt system.

13. The apparatus of claim 1, further comprising an antenna in electrical communication with the system controller for communicating with the external programming device.

14. The apparatus of claim 13, wherein the antenna is configured to communicate with the external programming device via RF communication.

15. The apparatus of claim 13, wherein controller and antenna are disposed on an implant separate from the implantable shunt system.

16. The apparatus of claim 1, wherein the implantable shunt system further includes a second sensor element for measuring an additional physiological characteristic, the second sensor element being configured to transmit data representing the measured value of the additional physiological characteristic to the system controller.

17. The apparatus of claim 1, wherein the implantable shunt system further includes a battery for powering the system.

18. The apparatus of claim 1, wherein the external programming device is adapted to power the implantable shunt system.

19. A system for regulating fluid flow, comprising:
   a housing having an inlet port and an outlet port, the housing configured to carry a fluid between the inlet port and the outlet port;
   a valve coupled to the housing and in fluid communication with the inlet port and the outlet port, the valve having an electromechanical valve actuator mechanically coupled to the valve and adapted to adjust a resistance of the valve and thereby adjust a pressure threshold at which fluid begins to flow through the valve;
   an internal system controller in electrical communication with and adapted to operate the electromechanical valve actuator;
   a sensor element in communication with the system controller and adapted to measure a physiological characteristic of a patient; wherein the sensor element is a pressure sensor for detecting pressure variations within the ventricular cavity; and
   an external system controller adapted to communicate with the internal system controller and modify the operating parameters thereof.

20. The system of claim 19, wherein the valve is a ball valve.

21. The system of claim 20, wherein the electromechanical valve actuator comprises a spring operatively associated with a pressure setting mechanism, and at least one selected from the group consisting of an electric motor, a solenoid, and a linear actuator mechanically coupled to the pressure setting mechanism to vary a pressure applied by the spring to thereby adjust the resistance of the valve.

22. The system of claim 21, wherein the spring is a leaf spring.

23. The system of claim 21, wherein the spring is a helical spring.

24. The system of claim 19, further comprising an antenna in electrical communication with the internal system controller for communicating with the external system controller.

25. A method for regulating cerebrospinal fluid flow in a hydrocephalus patient, comprising:
- comparing a target value to a value detected by a sensor associated with an implantable shunt system; wherein the detected value is a physiological characteristic of the ventricular cavity; and
- activating an electromechanical valve actuator of the implantable shunt system to adjust a resistance of a valve of the shunt system if the detected value is not equal to the target value.

26. The method of claim 25, wherein detecting a value of a physiological characteristic comprises communicating data representative of the detected value of the physiological characteristic from the sensor element to a controller of the implantable shunt system.

27. The method of claim 26, further comprising generating an activation signal via the controller to activate the electromechanical valve actuator.

28. The method of claim 27, wherein generating an activation signal to activate the electromechanical valve actuator and adjust the resistance of the valve comprises determining a desired resistance to achieve the target value.

29. The method of claim 25, further comprising transmitting the target value to a controller of the implantable shunt system.

30. The method of claim 29, wherein the target value is transmitted via an external programming device.

31. The method of claim 30, further comprising inputting one or more target values to the external programming device.

32. The method of claim 30, further comprising energizing the implantable shunt system with the external programming device.

33. The method of claim 25, wherein activating the electromechanical valve actuator to adjust a resistance of the valve is repeated until the detected value is equal to the target value.

* * * * *